(12) United States Patent
Haas et al.

(10) Patent No.: US 10,450,590 B2
(45) Date of Patent: Oct. 22, 2019

(54) PROCESS FOR PREPARING AN ALPHA, OMEGA-ALKANEDIOL

(71) Applicants: Thomas Haas, Muenster (DE); Philip Engel, Essen (DE); Jan Christoph Pfeffer, Hanau (DE); Oliver Thum, Ratingen (DE); Christian Gehring, Marl (DE)

(72) Inventors: Thomas Haas, Muenster (DE); Philip Engel, Essen (DE); Jan Christoph Pfeffer, Hanau (DE); Oliver Thum, Ratingen (DE); Christian Gehring, Marl (DE)

(73) Assignee: Evonik Degussa GmbH, Essen (DE)

( * ) Notice: Subject to any disclaimer, the term of this patent is extended or adjusted under 35 U.S.C. 154(b) by 461 days.

(21) Appl. No.: 14/763,378

(22) PCT Filed: Jan. 10, 2014

(86) PCT No.: PCT/EP2014/050373
§ 371 (c)(1),
(2) Date: Jul. 24, 2015

(87) PCT Pub. No.: WO2014/114505
PCT Pub. Date: Jul. 31, 2014

(65) Prior Publication Data
US 2015/0353963 A1    Dec. 10, 2015

(30) Foreign Application Priority Data

Jan. 24, 2013 (EP) ..................................... 13152491

(51) Int. Cl.
*C12P 7/18* (2006.01)
*C07C 67/08* (2006.01)
*C07C 29/136* (2006.01)
*C12P 7/62* (2006.01)

(52) U.S. Cl.
CPC .............. *C12P 7/18* (2013.01); *C07C 29/136* (2013.01); *C07C 67/08* (2013.01); *C12P 7/62* (2013.01); *C12Y 114/15003* (2013.01)

(58) Field of Classification Search
CPC ......... C07C 29/136; C07C 67/08; C12P 7/18; C12P 7/62; C12Y 114/15003
See application file for complete search history.

(56) References Cited

U.S. PATENT DOCUMENTS

| | | | |
|---|---|---|---|
| 6,008,418 A | 12/1999 | Baur et al. | |
| 6,204,417 B1 * | 3/2001 | Fischer | B01J 23/56 568/853 |
| 6,764,671 B2 | 7/2004 | Haas et al. | |
| 7,005,528 B2 | 2/2006 | Haas et al. | |
| 7,030,052 B2 | 4/2006 | Stochniol et al. | |
| 7,091,384 B2 | 8/2006 | Jaeger et al. | |
| 7,507,862 B2 | 3/2009 | Stochniol et al. | |
| 7,754,778 B2 | 7/2010 | Knott et al. | |
| 7,923,225 B2 | 4/2011 | Mueller et al. | |
| 8,349,596 B2 | 1/2013 | Mueller et al. | |
| 8,349,907 B2 | 1/2013 | Henning et al. | |
| 8,378,127 B2 | 2/2013 | Dingerdissen et al. | |
| 8,404,470 B2 | 3/2013 | Thum et al. | |
| 8,486,677 B2 | 7/2013 | Thum et al. | |
| 8,703,451 B2 | 4/2014 | Haas et al. | |
| 8,796,000 B2 | 8/2014 | Thum et al. | |
| 8,835,691 B2 | 9/2014 | Klasovsky et al. | |
| 8,927,773 B2 | 1/2015 | Klasovsky et al. | |
| 8,946,463 B2 | 2/2015 | Klasovsky et al. | |
| 8,981,159 B2 | 3/2015 | Klasovsky et al. | |
| 8,999,684 B2 | 4/2015 | Poetter et al. | |
| 9,012,227 B2 | 4/2015 | Karau et al. | |
| 2003/0212298 A1 | 11/2003 | Brasse et al. | |
| 2010/0248325 A1 | 9/2010 | Eckstein et al. | |
| 2010/0324257 A1 * | 12/2010 | Karau | C08G 69/08 528/310 |
| 2011/0118433 A1 | 5/2011 | Pötter et al. | |
| 2011/0118504 A1 | 5/2011 | Haas et al. | |
| 2011/0171702 A1 | 7/2011 | Reinecke et al. | |
| 2012/0034665 A1 | 2/2012 | Haas et al. | |
| 2013/0052700 A1 * | 2/2013 | Poetter | C07K 14/21 435/128 |

(Continued)

FOREIGN PATENT DOCUMENTS

DE    197 20 657 A1    11/1998
EP    2 322 598 A2    5/2011

(Continued)

OTHER PUBLICATIONS

Nie et al. (2014) Scientific Reports 4 (article 4968): 1-11.*

(Continued)

*Primary Examiner* — Lisa J Hobbs
(74) *Attorney, Agent, or Firm* — Oblon, McClelland, Maier & Neustadt, L.L.P.

(57) ABSTRACT

The invention relates to a process for preparing an α,ω-alkanediol comprising the steps of a) reacting an alkanoic acid with an alkanol to give an ester, b) oxidizing at least one terminal carbon atom of the ester by contacting with a whole-cell catalyst, which expresses an alkane hydroxylase, in aqueous solution and in the presence of molecular oxygen, to give an oxidized ester, c) hydrogenating the oxidized ester to form the alkanediol and alkanol, and d) removing the alkanol by distillation, forming a reaction mixture depleted with respect to the alkanol, and recycling the alkanol in step b).

16 Claims, 3 Drawing Sheets
Specification includes a Sequence Listing.

(56) References Cited

U.S. PATENT DOCUMENTS

| | | |
|---|---|---|
| 2013/0164797 A1 | 6/2013 | Gielen et al. |
| 2013/0183725 A1 | 7/2013 | Poetter et al. |
| 2014/0039071 A1 | 2/2014 | Thum et al. |
| 2014/0039210 A1 | 2/2014 | Erhardt et al. |
| 2014/0054224 A1 | 2/2014 | Erhardt et al. |
| 2014/0120587 A1 | 5/2014 | Haas et al. |
| 2014/0178948 A1 | 6/2014 | Schaffer et al. |
| 2014/0186905 A1 | 7/2014 | Schaffer et al. |
| 2014/0242646 A1 | 8/2014 | Pötter et al. |
| 2014/0256904 A1 | 9/2014 | Schaffer et al. |
| 2014/0308717 A1 | 10/2014 | Haas et al. |
| 2015/0010968 A1 | 1/2015 | Engel et al. |
| 2015/0044744 A1 | 2/2015 | Pfeffer et al. |
| 2015/0099282 A1 | 4/2015 | Haas et al. |
| 2015/0111253 A1 | 4/2015 | Schaffer et al. |
| 2015/0111254 A1 | 4/2015 | Hennemann et al. |
| 2015/0125912 A1 | 5/2015 | Haas et al. |
| 2015/0203629 A1 | 7/2015 | Ortelt et al. |
| 2015/0209775 A1 | 7/2015 | Erhardt et al. |
| 2015/0218600 A1 | 8/2015 | Haas et al. |
| 2015/0267231 A1 | 9/2015 | Haas et al. |
| 2015/0275245 A1 | 10/2015 | Haas et al. |
| 2015/0284747 A1 | 10/2015 | Schiemann et al. |

FOREIGN PATENT DOCUMENTS

| | | |
|---|---|---|
| EP | 2 322 598 A3 | 5/2011 |
| EP | 2 602 329 A1 | 6/2013 |
| WO | WO 97/31882 A1 | 9/1997 |
| WO | WO 2009/077461 A1 | 6/2009 |
| WO | WO 2011/131420 A1 | 10/2011 |
| WO | WO 2012/110125 A1 | 8/2012 |
| WO | WO 2013/083412 A1 | 6/2013 |
| WO | WO 2013/135650 A1 | 9/2013 |
| WO | WO 2014/029577 A1 | 2/2014 |
| WO | WO 2014/079683 A1 | 5/2014 |
| WO | WO 2015/028423 A1 | 3/2015 |

OTHER PUBLICATIONS

Fuji et al. (2006) Biosci. Biotech. Biochem. 70(6): 1379-1385. (Year: 2006).*

European Search Report dated Jul. 1, 2013 in Patent Application No. 13 152 491.0 (with English translation of categories of cited documents).

International Search Report dated Feb. 11, 2014 in PCT/EP2014/050373.

* cited by examiner

PROCESS FOR PREPARING AN ALPHA, OMEGA-ALKANEDIOL

The invention relates to a process for preparing an α,ω-alkanediol comprising the steps of a) reacting an alkanoic acid with an alkanol to give an ester, b) oxidizing at least one terminal carbon atom of the ester by contacting with a whole-cell catalyst, which expresses an alkane hydroxylase, in aqueous solution and in the presence of molecular oxygen, to give an oxidized ester, c) hydrogenating the oxidized ester to form an α,ω-alkanediol and an alkanol, and d) removing the alkanol by distillation, forming a reaction mixture depleted with respect to the alkanol, and recycling the alkanol in step a).

Amines and diamines are a class of molecules in high demand industrially, which are obtained conventionally during cracking of hydrocarbons. They are used, for example, for preparing polyamides and synthetic, commercially available, thermoplastics.

The conventional chemical-technical production of amines and diamines is dependent on the supply of fossil raw materials, inefficient, and in the process large amounts of undesired by-products are produced. In view of the said disadvantages, processes have been developed in order to obtain amines using biocatalysts starting from renewable raw materials. Alkanes or alkanols in particular are useful as reactants, which can be prepared by biotechnological processes from renewable raw materials. Various methods for converting alkanes and alkanols to amines are described in the prior art, for example, in the European patent applications EP11174729.1 and EP11006458.1.

A disadvantage of the methods described in the prior art is that only part of the alkane or alkanol used as reactant is converted to the product. A considerable portion reacts to give undesirable by-products or intermediates or remains unreacted in the reaction mixture.

Against this background, the problem on which the invention is based consists of providing a process for preparing an α,ω-alkanediol, in which the highest possible proportion of alkanol used as reactant is incorporated in the desired product, preferably the α,ω-alkanediol of interest.

These and further objects are achieved by the subject matter of the present application and in particular also by the subject matter of the accompanying independent claims, the dependent claims specifying embodiments of the invention.

The problem on which the invention is based is solved in a first aspect by a process comprising the steps of:
a) reacting an alkanoic acid with an alkanol to give an ester,
b) oxidizing at least one terminal carbon atom of the ester by contacting with a whole-cell catalyst, which expresses an alkane hydroxylase, in aqueous solution and in the presence of molecular oxygen, to give an oxidized ester,
c) hydrogenating the oxidized ester to form an α,ω-alkanediol and an alkanol,
d) removing the alkanol by distillation, forming a reaction mixture depleted with respect to the alkanol, and
e) recycling the alkanol in step a).

In a first embodiment of the first aspect, the problem is solved by a process wherein the alkanoic acid in step a) is an alkanoic acid of the formula $H_3C-(CH_2)_n-COOH$, and where n>0, preferably 2 to 16.

In a second embodiment of the first aspect, which also represents an embodiment of the first embodiment, the problem is solved by a process wherein the alkanoic acid is butanoic acid.

In a third embodiment of the first aspect, which also represents an embodiment of the first and second embodiments, the problem is solved by a process wherein the alkanoic acid in step a) is a carboxylated cycloalkane of the formula $C_nH_{2n-1}COOH$, where n>4, preferably 5 to 8.

In a fourth embodiment of the first aspect, which also represents an embodiment of the first to the third embodiment, the problem is solved by a process wherein the alkanol is an alkanol of the formula $C_nOH_{2n+2}$, and where n>0.

In a fifth embodiment of the first aspect, which also represents an embodiment of the first to the fourth embodiment, the problem is solved by a process wherein the alkanoic acid and the alkanol in step a) have the same carbon skeleton.

In a sixth embodiment of the first aspect, which also represents an embodiment of the first to the fifth embodiment, the problem is solved by a process wherein the whole-cell catalyst in step a) and/or c) expresses an alkane hydroxylase selected from the group comprising AlkB from *Pseudomonas putida* and variants thereof and CYP153 from *Alcanivorans borkumensis* SK2 and variants thereof.

In a seventh embodiment of the first aspect, which also represents an embodiment of the first to the sixth embodiment, the problem is solved by a process wherein step a) is carried out by means of acid-catalysed ester formation, preferably in the presence of an organic solvent.

In an eighth embodiment of the first aspect, which also represents an embodiment of the first to the seventh embodiment, the problem is solved by a process wherein step a) is carried out in aqueous solution by means of contacting with an esterase, protease or lipase, preferably provided in the form of a whole-cell catalyst expressing the esterase or lipase.

In a ninth embodiment of the first aspect, which also represents an embodiment of the first to the seventh embodiment, the problem is solved by a process wherein the alkanoic acid in step a) is provided by oxidizing an alkane to the alkanoic acid.

The process according to the invention firstly provides in step a) the reaction of an alkanoic acid with an alkanol to give an ester. Suitable reaction conditions for this are known to a person skilled in the art. For example, the esterification may be carried out directly using acid catalysis. In this case, the ester is preferably removed by distillation from the equilibrium with acid and alcohol. The alkanol is preferably an alkanol of the formula $C_nOH_{2n+2}$, where n is greater than 0 and preferably 1 to 4, most preferably 4 and by way of example 1, 2, 3, 4, 5, 6, 7, 8, 9, 10, 11, 12, 13, 14, 15, 16, 17, 18, 19, 20, 21 or 22.

Step a) is preferably carried out in the presence of an organic solvent. Particularly suitable as solvent are secondary and tertiary alcohols, particularly branched alcohols such as 2-methyl-2-butanol. Also suitable are ethers such as tert-butyl methyl ether or cycloalkanes such as hexane and methylhexane or aromatic solvents such as toluene.

In a preferred embodiment, step a) is carried out by contacting with a hydrolase, preferably from the group comprising esterase, protease or lipase. Suitable hydrolases are described in the prior art. Particularly suitable is, for example, the lipase Novozym® 435 from Novozymes.

After step a), step b) is conducted by oxidizing at least one terminal carbon atom of the ester by contacting with a whole-cell catalyst, which expresses an alkane hydroxylase, in aqueous solution and in the presence of molecular oxygen, to give an oxidized ester. In a preferred embodiment, the term "whole-cell catalyst", as used herein, is understood as meaning an intact, viable and metabolically active cell which provides the desired enzymatic activity of the alkane hydroxylase. The whole - cell catalyst is preferably a prokaryotic, preferably a bacterial cell. In a further preferred embodiment, said cell is a mammalian cell. In a further preferred embodiment, it is a lower eukaryotic cell, preferably a yeast cell. Examples of prokaryotic cells include *Escherichia*, particularly *Escherichia coli*, and strains of the genus *Pseudomonas* and *Corynebacterium*. Examples of lower eukaryotic cells include the genera *Saccharomyces, Candida, Pichia, Yarrowia, Schizosaccharomyces*, particularly the strains *Candida tropicalis, Schizosaccharomyces pombe, Pichia pastoris, Yarrowia lipolytica* and *Saccharomyces cerevisiae*. Suitable whole-cell catalysts, routes for the preparation thereof by genetic engineering methods and procedures for culturing are known to those skilled in the art.

For the oxidation in step b) it is essential that the whole-call catalyst has an alkane hydroxylase. It is furthermore advantageous if the whole-cell catalyst according to the invention has further enzymes favourable for the activity of the alkane hydroxylase. In a preferred embodiment, the term "alkane hydroxylase", as used herein, is understood to mean an enzyme which catalyses the hydroxylation of unsubstituted linear alkyl radicals comprising at least six, preferably twelve, carbon radicals. Oxidation systems are described by way of example, inter alia, in PCT/EP 2008/067447.

The alkane hydroxylase is preferably a cytochrome P450 monooxygenase of the GYP153 family. In a preferred embodiment, the term "cytochrome P450 monooxygenase of the CYP153 family" is understood to mean a cytosolic oxidase which is part of a 3-component system which further comprises a ferredoxin and a ferredoxin reductase, with an alkane binding site and the ability to hydroxylate alkanes. In a particularly preferred embodiment, it is an enzyme which has at least 80, preferably 90, most preferably 95 or 99%, sequence identity to the cytochrome P450 monooxygenase of the CYP153 family from *Alcanivorax borkumensis* SK2 (database code YP_691921 (SEQ ID NO: 2)), or an enzyme which comprises a polypeptide sequence which has at least 80, preferably 90, most preferably 95 or 99%, sequence identity to the cytochrome P450 monooxygenase of the CYP153 family from *Alcanivorax borkumensis* SK2 (database code YP_691921) and moreover has alkane hydroxylase activity. As throughout this application, the stated database codes concern the NCBI (National Center for Biotechnology Information, Bethesda, USA) databases, specifically the version available online on 11 Jan. 2013. In a preferred embodiment, the term "cytochrome P450 monooxygenase of the CYP153 family" is understood to mean a non-membrane-bound oxidase which a binding site for alkanes, unsubstituted linear alkyl radicals comprising at least five, preferably twelve, carbon radicals or monohydroxylated alkanes and the polypeptide chain of which comprises the motif LL(I/L)(V/I)GGNDTTRN. In a preferred embodiment, a "cytochrome P450 monooxygenase of the GYP153 family", as used herein, is a cytochrome P450 monooxygenase of the CYP153 family from *Alcanivorax borkumensis* SK2 (database code YP_691921) or a variant thereof which preferably has alkane hydroxylase activity.

For the optimal supply of the cytochrome P450 monooxygenase of the CYP153 family with electrons from the reducing agent, preferably NADH, it is preferred that the alkane hydroxylase of the whole-cell catalyst is expressed together with both ferredoxin reductase that interacts functionally with it and ferredoxin that interacts functionally with it. These take the form of coexpressed polypeptides or polypeptides fused on the N- or C-terminus with the cytochrome P450 monooxygenase of the CYP153 family. Whether a ferredoxin reductase or a ferredoxin interacts functionally with a given cytochrome P450 monooxygenase of the CYP153 family can be readily established by the person skilled in the art by whether the reducing agent is oxidized more efficiently in the presence of an alkane substrate and the three polypeptides than when at least one of the three is absent. Alternatively, it is possible to use the enzyme test described by Scheps, D., Malca, H., Hoffmann, B., Nestl, B. M, and Hauer, B. (2011) *Org. Biomol. Chem.*, 9, 6727, which, in the case of functionally interacting polypeptides, exhibits a considerable increase in the reaction rate. In a particularly preferred embodiment, the cytochrome P450 monooxygenase of the CYP153 family, the ferredoxin and the ferredoxin reductase originate from the same organism. In a particularly preferred embodiment, they are the ferredoxin reductase from *Alcanivorax borkumensis* SK2 (database code YP_691923) or a variant thereof, the ferredoxin from *Alcanivorax borkumensis* SK2 (database code YP_691920) or a variant thereof and the cytochrome P450 monooxygenase of the CYP153 family from *Alcanivorax borkumensis* SK2 (database code YP_691921) or a variant thereof.

In a further preferred embodiment, the alkane hydroxylase is an AlkB monooxygenase. AlkB represents an oxidoreductase which initially became known from the AlkBGT system of *Pseudomonas putida* Gpo1, and which is dependent on two further polypeptides, AlkG and AlkT. AlkT is characterized as an FAD-dependent rubredoxin reductase which transfers electrons from NADH to AlkG. AlkG is a rubredoxin, an iron-containing redox protein which functions as a direct electron donor to AlkB. In a preferred embodiment, the term "AlkB monooxygenase" is a polypeptide having a sequence homology of at least 75, 80, 85, 90, 92, 94, 96, 98 or 99%—specified in order of increasing preference—to the sequence of the AlkB of *Pseudomonas putida* Gpo1 (database code: CAB54050.1 (SEQ ID NO: 1); this databank code originates like all others from the prior art used in the application, namely from the NCBI database, more precisely the release available online on 11 Jan. 2013) having the capability to oxidize alkanes. In a particularly preferred embodiment, the AlkB monooxygenase is an oxidoreductase which functionally interacts with the AlkG (CAB54052.1) and AlkT (CAB54063.1) polypeptides from *Pseudomonas putida* Gpo1 and oxidizes alkanes. For the optimal supply of the AlkB alkane hydroxylase with electrons, it is preferred that the cell the alkane hydroxylase is expressed together with auxiliary proteins that interact functionally with it, preferably AlkG and/or AlkT or variants of each, and in a particularly preferred embodiment they are again AlkG (CAB54052.1) and AlkT (CAB54063.1) polypeptides from *Pseudomonas putida* Gpo1.

The whole-cell catalyst applicable for the oxidation in step b) can also be used to provide the alkanoic acid in step b). This is preferably accomplished by contacting the whole-cell catalyst with an alkane of the desired chain length for the alkanoic acid. In this case, the whole-cell catalyst must express an alkane hydroxylase which is capable of oxidizing the terminal carbon atom of an alkane up to the carboxyl group.

The teaching of the present invention can be carried out by not only using macromolecules having the exact amino acid or nucleic acid sequence to which reference is made herein or by not only using a cell having reduced activity, relative to the respective wild type, of a polypeptide having the exact amino acid sequence to which reference is made herein, but also by using a variant of such macromolecules or of a cell having a reduced activity, relative to the respective wild type of the respective cell, of a variant of the polypeptide, which variant can be obtained by deletion, addition or substitution of one or more than one amino acid or nucleic acid. In a preferred embodiment, the term "variant" of a nucleic acid sequence or amino acid sequence, used hereinafter synonymously and exchangeably with the term "homologue", as used herein, means another nucleic acid or amino acid sequence comprising or representing a sequence which, with respect to the corresponding original wild-type nucleic acid or amino acid sequence, has a homology, used here synonymously with identity, of 70, 75, 80, 85, 90, 92, 94, 96, 98, 99% or greater, wherein preferably amino acids other than the ones forming the catalytically active site or essential for the structure, activity or folding are deleted or substituted or are merely conservatively substituted, for example a glutamate instead of an aspartate or a leucine instead of a valine. The prior art describes algorithms, which may be used to calculate the degree of homology of two sequences, e.g. Arthur Lesk (2008), Introduction to Bioinformatics, $3^{rd}$ edition. In a further more preferred embodiment of the present invention, the variant of an amino acid or nucleic acid sequence, preferably in addition to the sequence homology mentioned above, has substantially the same enzymatic activity of the wild-type molecule and/or of the original molecule. For example, a variant of an enzymatically active polypeptide as protease has the same, or substantially the same, proteolytic activity as the polypeptide enzyme, i.e. the capability to catalyse the hydrolysis of a peptide bond. In a particular embodiment, the term "substantially the same enzymatic activity" means an activity, with respect to the substrates of the wild-type polypeptide, which clearly lies above the background activity or/and differs from the $K_M$ and/or $k_{cat}$ values by less than 3, more preferably 2, even more preferably one order of magnitude, which the wild-type polypeptide exhibits with respect to the same substrates. In a further preferred embodiment, the term "variant" of a nucleic acid or amino acid sequence includes at least one active part or fragment of the nucleic acid or amino acid sequence. In a further preferred embodiment, the term "active part", as used herein, means an amino acid sequence or a nucleic acid sequence which has a smaller amino acid sequence than the full length of the amino acid sequence or encodes a smaller amino acid sequence than the full length of the amino acid sequence, where the amino acid sequence or the encoded amino acid sequence with the smaller length than the wild-type amino acid sequence has substantially the same enzymatic activity as the wild-type polypeptide or a variant thereof, for example as protease. In a particular embodiment, the term "variant" of a nucleic acid encompasses a nucleic acid, the complementary strand of which, preferably under stringent conditions, binds to the wild-type nucleic acid. The stringency of the hybridization reaction is readily determinable by those skilled in the art and depends in general on the length of the probe, the washing temperatures and the salt concentration. Generally, longer probes require higher temperatures for the hybridization, whereas shorter probes work at low temperatures. Whether hybridization takes place depends in general on the capability of the denatured DNA to anneal to complementary strands which are present in its environment and below the melting temperature. The stringency of the hybridization reaction and corresponding conditions are described in detail in F M Ausubel (1995), Current Protocols in Molecular Biology. John Wiley & Sons, Inc. Instructions for identifying DNA sequences by means of hybridization can be found by the person skilled in the art inter alia in the handbook "The DIG System Users Guide for Filter Hybridization" from Boehringer Mannheim GmbH (Mannheim, Germany, 1993) and in Liebl et al. (International Journal of Systematic Bacteriology 41: 255-260 (1991)). The hybridization takes place in a preferred embodiment under stringent conditions, i.e. only hybrids are formed in which the probe and target sequence, i.e. the polynucleotides treated with the probe, are at least 70% identical. It is known that the stringency of the hybridization including the washing steps is influenced and/or determined by varying the buffer composition, the temperature and the salt concentration. The hybridization reaction is generally carried out at a relatively low stringency compared to the washing steps (Hybaid Hybridisation Guide, Hybaid Limited, Teddington, UK, 1996). For the hybridization reaction, for example, a buffer corresponding to 5×SSC buffer can be used at a temperature of about 50° C.-68° C. In this connection, probes can also hybridize with polynucleotides which have less than 70% identity to the sequence of the probe. Such hybrids are less stable and are removed by washing under stringent conditions. This can be achieved for example by lowering the salt concentration to 2×SSC and optionally subsequently 0.5×SSC (The DIG System User's Guide for Filter Hybridisation, Boehringer Mannheim, Mannheim, Germany, 1995), in which case a temperature of, increasing in order of preference, about 50° C.-68° C., about 52° C.-68° C., about 54° C.-68° C., about 56° C.-68° C., about 58° C.-68° C., about 60° C.-68° C., about 62° C.-68° C., about 64° C.-68° C., about 66° C.-68° C. is established. Temperature ranges from about 64° C.-68° C. or about 66° C.-68° C. are preferred. It is optionally possible to reduce the salt concentration down to a concentration corresponding to 0.2×SSC or 0.1×SSC. By means of a stepwise increase in the hybridization temperature in steps of about 1-2° C. from 50° C. to 68° C., polynucleotide fragments can be isolated which, for example in the order of increasing preference, at least 70% or at least 80% or at least 90%, at least 91%, at least 92%, at least 93%, at least 94%, at least 95%, at least 96%, at least 97%, at least 98% or at least 99% identity to the sequence of the nucleic acid molecule used. Further instructions relating to the hybridization are commercially available in the form of so-called kits (e.g. DIG Easy Hyb from Roche Diagnostics GmbH, Mannheim, Germany, Catalogue No. 1603558). In a preferred embodiment, the term "variant" of a nucleic acid, as used herein, encompasses any nucleic acid sequence which encodes the same amino acid sequence as the original nucleic acid or a variant of this amino acid sequence in the context of the degeneracy of the genetic code.

When using a whole-cell catalyst, the problem can arise that a substrate has to be brought into contact with an intracellularly localized enzyme so that it results in the desired reaction. In the case of long-chain alkanes and derivatives thereof, it is preferred that the whole-cell catalyst has a polypeptide of the AlkL family. In a preferred embodiment, a "polypeptide of the AlkL family", as used herein, is a polypeptide which, over a length of 230 successive amino acids, has an at least 80, preferably 90, more preferred 90% sequence identity to AlkL from *Pseudomonas putida* (database code CAB69081) and preferably the ability to assist the import of long-chain alkanes into the inside of a cell. In a further embodiment, a "polypeptide of the AlkL family", as used herein, is a polypeptide located in the outer membrane of a Gram-negative bacterium and which has the sequence motif DXWAPAXQ(V/A)GXR, where X is a proteinogenic amino acid, and preferably is additionally AlkL from *Pseudomonas putida* (database code CAB69081) or a variant thereof. Examples of members of the AlkL family include AlkL from *Pseudomonas putida* (database code CAB69081), *Marinobacter aquaeolei* VT8 (database code YP_957722), *Oceanicaulis alexandrii* HTCC2633 (database code ZP_00953584), *Marinobacter manganoxydans* Mnl7-9 (database code ZP_09158756), *Caulobacter* sp. K31 (database code YP_001672217), *Pseudomonas oleovorans* (database code Q00595) and variants thereof.

Also if the invention can be performed using unchanged wild-type strains of whole-cell catalysts having an alkane hydroxylase, it is preferable that the enzymes used in accordance with the invention are recombinant enzymes expressed in the whole-cell catalyst. In a preferred embodiment, the term "recombinant", as used herein, is understood as meaning that the coding nucleic acid molecule does not occur in nature and/or it has been produced using genetic engineering methods. In a preferred embodiment, the term recombinant protein is used if the corresponding polypeptide is encoded by a recombinant nucleic acid. In a preferred embodiment, a recombinant cell, as used herein, is understood to mean a cell which has at least one recombinant nucleic acid or one recombinant polypeptide. Processes suitable for producing recombinant molecules or cells are known to the person skilled in the art, for example those described in Sambrook/Fritsch/Maniatis (1989): Molecular Cloning: A Laboratory Manual, Cold Spring Harbor Laboratory Press, 2nd edition.

Molecular oxygen ($O_2$) must be present as substrate for the alkane hydroxylase in step b). This is preferably achieved by access of atmospheric air to the aqueous solution in which step b) proceeds. The aqueous solution is preferably stirred under aeration.

As aqueous solution it is possible to use any solution based on water which is compatible with the activity of the whole-cell catalyst. This is preferably in the form of an aqueous medium, particularly preferably a minimal medium, which maintains the metabolic activity of the whole-cell catalyst but which comprises the fewest possible further substances, besides the reactants, which would impair obtaining the reaction product in pure form. For example, M9 medium can be used.

The alkanoic acid can be any organic compound bearing a carboxyl group on an alkyl residue which can be esterified. Particular preference is given to an alkanoic acid of the formula $H_3C-(CH_2)_n-COOH$, where n is 0 or greater, preferably 2 to 24, particularly preferably 2 to 16, most preferably 4, by way of example 0, 1, 2, 3, 4, 5, 6, 7, 8, 9, 10, 11, 12, 13, 14, 15, 16, 17, 18, 19, 20, 21, 22, 23 or 24. In a further preferred embodiment, the alkanoic acid is a carboxylated cycloalkane of the formula $C_nH_{2n-1}COOH$, where n is 5, 6, 7, 8, 9, 10, 11, 12, 13, 14, 15, 16, 17, 18, 19, 20, 21, 22, 23 or 24, and preferably 5 to 8.

With respect to the alkanoic acid and to any chemical compound described in this application, it is the case that the respective specified formula encompasses all salts, protonated or deprotonated, of the respective compound. For example, the butanoic acid encompasses not only the protonated form, but also the butyrate salt with all cations, for example sodium butyrate.

Step c) of the process according to the invention comprises the hydrogenation of the oxidized ester to form the alkanediol and alkanol. In the prior art, in the patent applications WO97/31882 and EP1042259B1 for example, numerous suitable hydrogenation methods are described, for example using ZnO/CuO, Ru- or Rh-containing catalysts, which with inorganic hydrides such as $LiAlH_4$.

Step d) of the process according to the invention comprises removing the alkanol by distillation, forming a reaction mixture depleted with respect to the alkanol. The reaction mixture comprises the alkanediol product which can be subsequently separated from the medium and from the whole-cell catalyst by further separation and washing steps.

The final step of the method comprises the recycling of the alkanol removed in step d) into step a), i.e. the alkanol is reacted with further alkanoic acid and is therefore conserved in the process.

The present invention is more particularly described by the following figures and non-limiting examples from which further features, embodiments, aspects and advantages of the present invention may be discerned.

EXAMPLE 1

Figure 1:
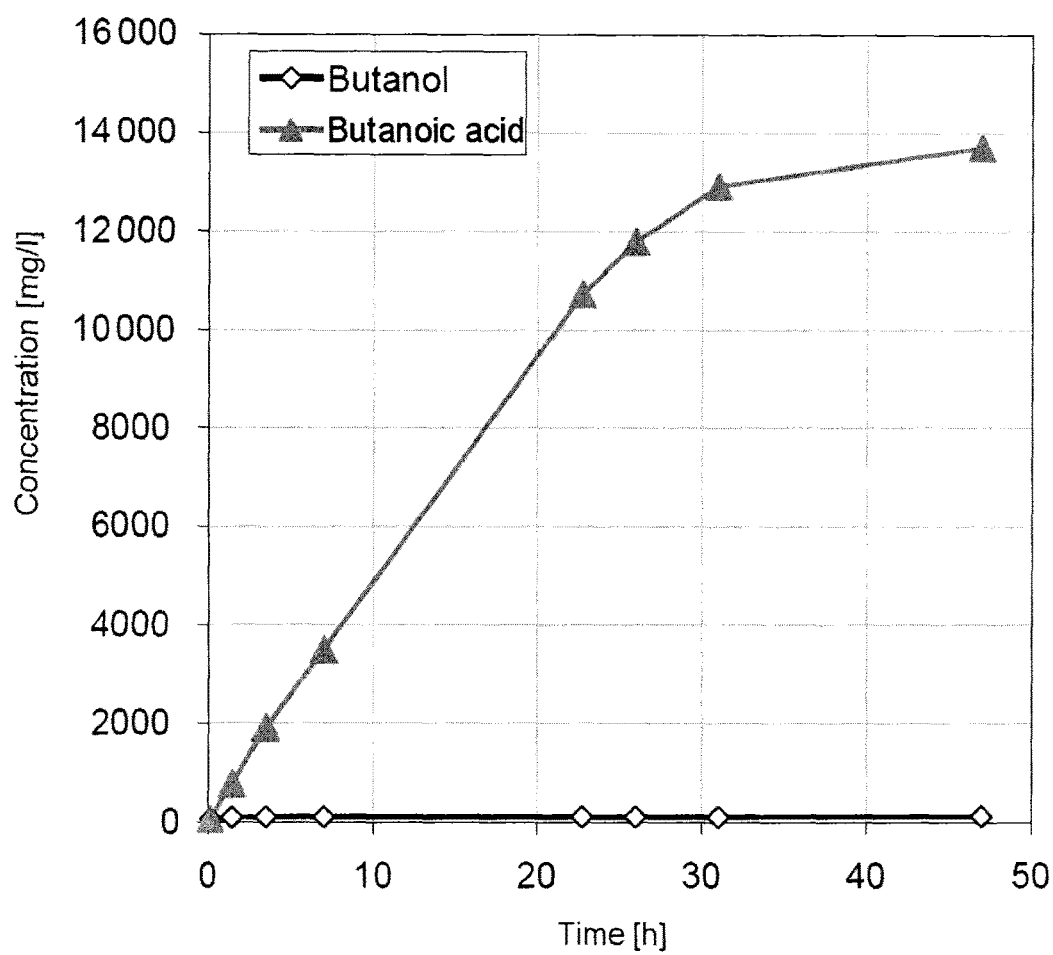
FIG. 1 shows the time course of the butanoic acid and 1-butanol concentration in the biotransformation of n-butane with *E. coli* W3110 pBT10, resulting from the procedure of Example 1.

Oxidation of n-butane by *E. coli* W3110 pBT10 with the Monooxygenase (alkBGT) from *P. putida* GPO1 a) Production of Biomass on a 10 l Scale

Preseed culture: 1 liter of LB Medium (5 g/l yeast extract, 10 g/l peptone, 0.5 g/l NaCl, dissolved in 1 l of water, autoclaved for 20 minutes at 121° C.) was prepared.

From this solution, 5×25 ml were each filled in 100 ml shaking flasks with chicanes, 25 µl of a sterile-filtered kanamycin solution (50 g/l) were added to each flask and in each case inoculated with 200 µl of a glycerol cryoculture of *E. coli* W3110 pBT10. The strain comprising the plasmid pBT10 is already described in detail in Example 4 of WO13083412. These cultures were incubated for 18 h at 37° C. and 200 rpm (amplitude 2.5 cm).

Seed culture: 1 liter of high cell density medium (HCD medium) was prepared, consisting of 1.76 g/l $NH_4SO_4$, 19.08 g/l $K_2HPO_4$, 12.5 g/l $KH_2PO_4$, 6.66 g/l yeast extract, 1.96 g/l $Na_3$-citrate, 17 ml of $NH_4Fe$-citrate solution (1%), 5 ml of trace element solution US3 (1 liter of the trace element solution US 3 is composed of 36.5 g of HCl 37%, 1.91 g of $MnCl_2×4H_2O$, 1.87 g of $ZnSO_4×7H_2O$, 0.8 g of Na-EDTA×$2H_2O$, 0.3 g of $H_3BO_3$, 0.25 g of $Na_2MoO_4×2H_2O$, 4.7 g of $CaCl_2×2H_2O$, 17.8 g of $FeSO_4×7 H_2O$, 0.15 g of $CuCl_2×2H_2O$, dissolved in 1 l of water), 30 ml of feed solution (glucose 50% w/v, $MgSO_4×7 H_2O$ 0.5% w/v, $NH_4Cl$ 2.2% w/v), and 1 ml of kanamycin solution (50 g/l). 948 ml of the solution with $NH_4SO_4$ to $Na_3$-citrate were autoclaved and the remainder was separately sterile filtered and then added under sterile conditions. The pH was 6.8.

5×75 ml of the HCD medium were added to 1000 ml shaking flasks with chicanes, each was inoculated with 25 ml of preseed culture and cultured at 37° C. and 200 rpm (amplitude 2.5 cm) for 30 h.

A sterile 10 l fermenter was filled with 7 l of a sterile medium having the composition of 1.75 g/l $(NH_4)_2SO_4$, 19 g/l $K_2HPO_4 \times 3\ H_2O$, 12.5 g/l $KH_2PO_4$, 6.6 g/l yeast extract, 2.24 g/l $Na_3$-citrate$\times 2H_2O$, 15 g/l glucose, 0.49 g/l $MgSO_4 \times 7\ H_2O$, 16.6 ml/l $NH_4Fe$-citrate solution (1% w/v), 15 ml/l trace element solution (as in the seed culture), 1 ml/l kanamycin solution (50 mg/l) and 2 ml of antifoaming agent Delamex. The feed was an autoclaved solution of glucose (50% w/v) supplemented with $MgSO_4 \times 7H_2O$ 10 g/l, corrected for pH with 0.5M $H_2SO_4$ and 25% $NH_4OH$.

The cultures from the shaking flasks were combined under sterile conditions and inoculated into the fermenter via a transfer bottle. The fermentation conditions were adjusted to $pO_2$ 30%, airflow 6 nlpm, stirrer 400-1200 rpm, temperature 37° C., pH 7, feed start 8 h, feed rate 150-250 g/h. After 19 h, the temperature was reduced to 30° C. and the mixture was induced with 0.4 mM DCPK. After 23 hours, the OD600 in the fermenter was ca.100, the culture broth was removed under sterile conditions and 500 ml in 1000 ml centrifuge flasks were centrifuged at 8000 rpm. The supernatant was discarded and the pellets were aliquoted into Falcon tubes each with 10 g. The pellets were frozen at −80° C. for later use.

b) Oxidation of n-butane to 1-butanol and Butanoic Acid 10 g of the frozen biomass as described in a) were resuspended in 50 ml of 70 mM ammonium phosphate buffer pH 7 (composition: 8 g/l $(NH_4)H_2PO_4$, 0.5 g/l NaCl, 0.49 g/l $MgSO_4 \times 7H_2O$, 1 ml of trace element solution US3 and 50 µg/l kanamycin). The pH was adjusted in this case with 5% $NH_4OH$.

130 ml of 70 mM ammonium phosphate buffer pH 7 (composition: 8 g/l $(NH_4)H_2PO_4$, 0.5 g/l NaCl, 0.49 g/l $MgSO_4 \times 7H_2O$, 1 ml of trace element solution US3 and 50 µg/l kanamycin. pH adjusted to 7.0 with 5% ammonia solution.) with ca. 3 drops of autoclaved antifoam (Delamex) were charged in a 300 ml fermenter. The fermenter was flushed with a gas mixture consisting of 25% n-butane and 75% synthetic air via a metal sinter perlator having a pore size of 0.2 µm at a flow rate of 9 IN/h. The fermenter was heated to 30° C. in a water bath and stirred by means of a magnetic stirrer at 900 rpm. The pH was regulated to 7.0 with 2.5% ammonia solution. Glucose solution was fed in continuously (glucose feed rate of 0.9 g/lh). The exhaust gas was passed through an ice-cooled wash bottle containing 150 ml of water.

From the biomass frozen as described in a), 10 g were resuspended in 50 ml of ammonium phosphate buffer and thawed. The fermenter was inoculated with the suspension.

The biomass concentration had an optical density (600 nm) of 25.5 ml samples were removed at various time points from the fermenter. The samples were centrifuged at room temperature for 10 minutes at 10 000 g and the supernatant filtered through a 0.2 µm syringe filter unit.

The chromatographic analysis of butanoic acid and 1-butanol was conducted by HPLC-RID on an Agilent Technologies 1200 system. An Aminex HPX-87H column (300 mm×7.8 mm) was used. The system was operated using 10 mM $H_2SO_4$ as eluent at a flow rate of 0.6 ml/min and a column temperature of 40° C. Standards for all substances to be analysed were prepared in ultra-pure water and measured under identical conditions. The evaluation was performed by comparison of retention times.

After 48 h, the butanoic acid concentration was ca. 13.5 g/l and the 1-butanol concentration 0.125 g/l (see FIG. 1).

EXAMPLE 1C

Oxidation of n-butane by *E. coli* W3110 pBT10 with the Monooxygenase CYP153 from *Alcanivorax borkumensis*

Three 100 ml chicane flasks containing 25 ml of LB medium with kanamycin (composition: 5 g/l yeast extract, 10 g/l peptone, 0.5 g/l NaCl, 50 mg/l kanamycin sulphate) are each inoculated with 100 µl of a glycerol cryoculture of *E. coli* W3110 pCOM10[Ab_Fd/CYP153-2/FdOR/alkL] having the monooxygenase CYP153 from *Alcanivorax borkumensis* and are incubated at 37° C. and 200 rpm for 20 h. The strain used is described in detail in Example 4 in conjunction with Example 1 of PCT/EP2013/054928.

Each 25 ml of the culture broth are then used as inoculum in 75 ml of modified M9 medium (composition: 15 g/l glucose, 6.8 g/l $Na_2PO_4$, 3 g/l $KH_2PO_4$, 0.5 g/l NaCl, 2 g/l $NH_4Cl$, 15 g/l yeast extract, 0.49 g/l $MgSO_4*7H_2O$, 50 mg/l kanamycin sulphate, 15 ml/l trace element solution US3. Composition of the trace element solution: 36.5 g/l 37% hydrochloric acid, 1.91 g/l $MnCl_2*4H_2O$, 1.87 g/l $ZnSO_4*7H_2O$, 0.84 g/l Na-EDTA*$2H_2O$, 0.3 g/l $H_3BO_3$, 0.25 g/l $Na_2MoO_4*2H_2O$, 4.7 g/l $CaCl_2*2H_2O$, 17.3 g/l $FeSO_4*7H_2O$, 0.15 g/l $CuCl_2*2H_2O$) in 1000 ml chicane flasks. The flasks are incubated at 37° C. and 200 rpm for 2.5 h. The temperature is then reduced to 25° C. The culture is induced after 0.5 hours at 25° C. with 0.4 mM dicyclopropyl ketone. The cultures are incubated at 25° C. and 200 rpm for a further 16 h.

The cultures are combined, transferred to 50 ml falcon tubes and centrifuged at 5500 g at 25° C. for 10 minutes. The supernatant is discarded and the pellets from 300 ml of culture are resuspended in 50 ml of conversion buffer pH 7. (Composition: 8 g/l $(NH_4)H_2PO_4$, 0.5 g/l NaCl, 0.49 g/l $MgSO_4*7H_2O$, 50 mg/l kanamycin sulphate, 15 ml/l trace element solution US3; pH adjusted to 7.0 with 25% ammonia solution).

The transformation, sampling and analytics are conducted with *E. coli* W3110 pCOM10[Ab_Fd/CYP153-2/FdOR/alkL] analogously to 1.1.

The butanoic acid and the butanol from 1-b) and 1-c) are separated by distillation from the aqueous phase and used further in Example 1 d.

EXAMPLE 1D

Azeotropic Esterification of Butanoic Acid and Butanol 88 g of butanoic acid and 81.4 g of 1-butanol from Examples 1 b and 1c and in the case of butanol optionally from Example 3 and also 5 g of para-toluenesulphonic acid are mixed and heated to boiling. The reaction is carried out under reflux by means of azeotropic distillation using a water separator until the calculated quantity of water (18 mL) for quantitative conversion had been separated. The ester formed (129.6 g of butyl butyrate) is separated by distillation from excess 1-butanol and the catalyst and is transferred for the oxidation by the whole-cell catalyst in Example 2.

EXAMPLE 2

Oxidation of Butyl Butyrate

Each 100 ml chicane flask containing 25 ml of LB medium with kanamycin (composition: 5 g/l yeast extract, 10 g/l peptone, 0.5 g/l NaCl, 50 mg/l kanamycin sulphate) was inoculated with 100 μl of a glycerol cryoculture of *E. coli* W3110 pCOM10[Ab_Fd/CYP153-2/FdOR/alkL] or *E. coli* W3110 pBT10 and was incubated at 37° C. and 200 rpm for 20 h.

Each of the complete precultures was then used as inoculum in 75 ml of modified M9 medium (composition: 15 g/l glucose, 6.8 g/l $Na_2PO_4$, 3 g/l $KH_2PO_4$, 0.5 g/l NaCl, 2 g/l $NH_4Cl$, 15 g/l yeast extract, 0.49 g/l $MgSO_4*7H_2O$, 50 mg/l kanamycin sulphate, 15 ml/l trace element solution US3. Composition of the trace element solution: 36.5 g/l 37% hydrochloric acid, 1.91 g/l $MnCl_2*4H_2O$, 1.87 g/l $ZnSO_4*7H_2O$, 0.84 g/l $Na-EDTA*2H_2O$, 0.3 g/l $H_3BO_3$, 0.25 g/l $Na_2MoO_4*2H_2O$, 4.7 g/l $CaCl_2*2H_2O$, 17.3 g/l $FeSO_4*7H_2O$, 0.15 g/l-$CuCl_2*2H_2O$) in 1000 ml chicane flasks. The flasks were incubated at 37° C. and 200 rpm for 2.5 h. The temperature was then reduced to 25° C. The culture was induced after 0.5 hours with 0.4 mM dicyclopropyl ketone. The culture was incubated at 25° C. and 200 rpm for a further 16 h.

The cultures were transferred to 50 ml falcon tubes and centrifuged at 5500 g at 25° C. for 10 minutes. The supernatant was discarded and the pellets from each strain were resuspended in 50 ml of conversion buffer pH 7 (composition: 8 g/l $(NH_4)H_2PO_4$, 0.5 g/l NaCl, 0.49 g/l $MgSO_4*7H_2O$, 50 mg/l kanamycin sulphate, 15 ml/l trace element solution US3; pH adjusted to 7.0 with 25% ammonia solution) and incubated at 30° C. and 180 rpm in 500 ml chicane flasks.

In order to start the reaction, 2 g/l butyl butyrate and 5 g/l glucose were added to each flask. A flask with buffer, butyl butyrate and glucose without cells was incubated as a negative control.

The biomass concentration had an optical density (600 nm) of 2.5. A 2 ml sample was taken in each case after 10 min and 7 h. The samples were centrifuged at room temperature for 10 minutes at 10 000 g and the supernatant filtered through a 0.2 μm syringe filter unit.

Figure 2:
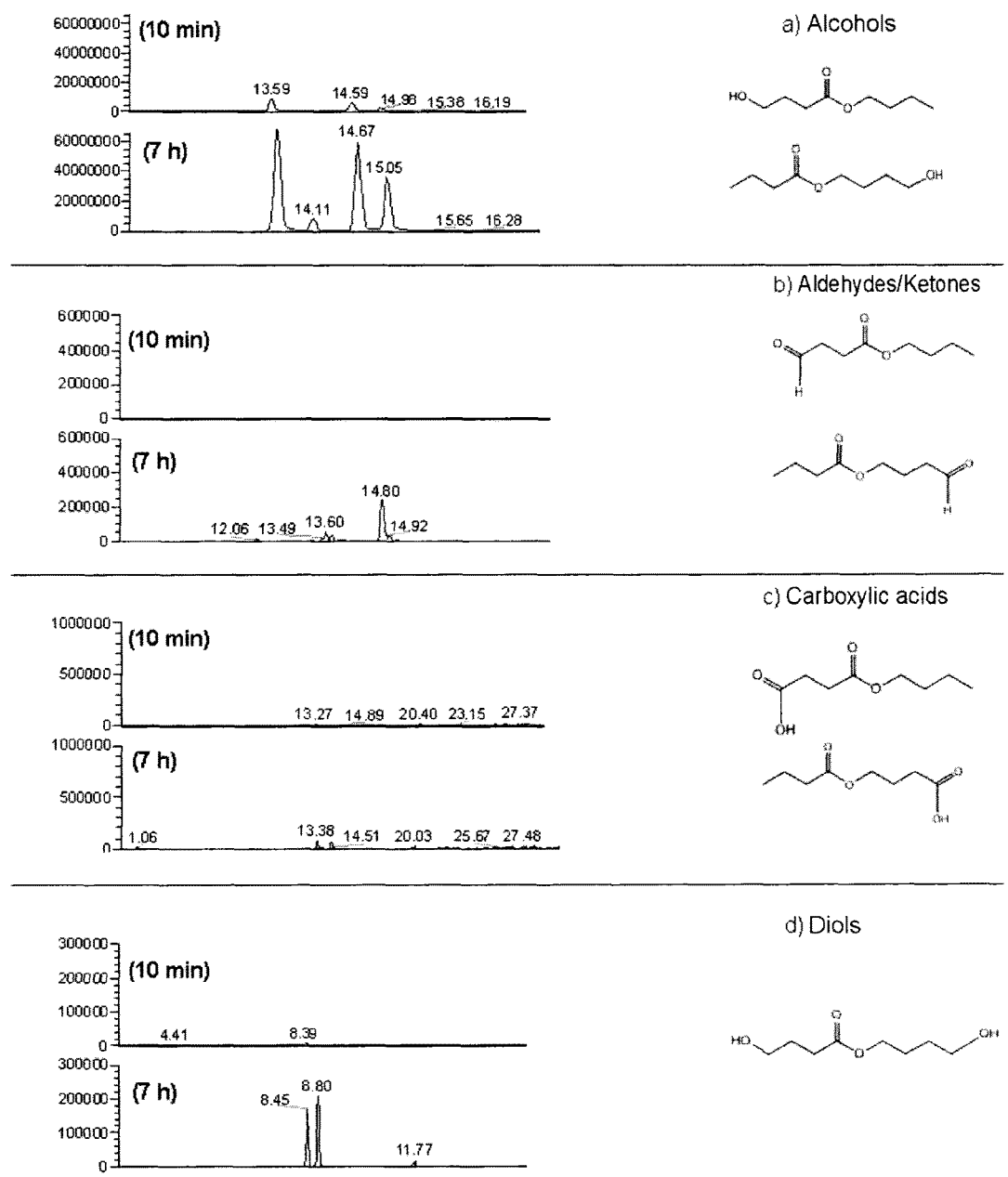
FIG. 2 shows the mass traces of the HPLC-MS analysis of the oxidation products of butyl butyrate using *E. coli* W3110 pCOM10[Ab_Fd/CYP153-2/FdOR/alkL] with a comparison of the 10 min sample with the 7 h sample, resulting from the procedure of Example 2.
Figure 3:
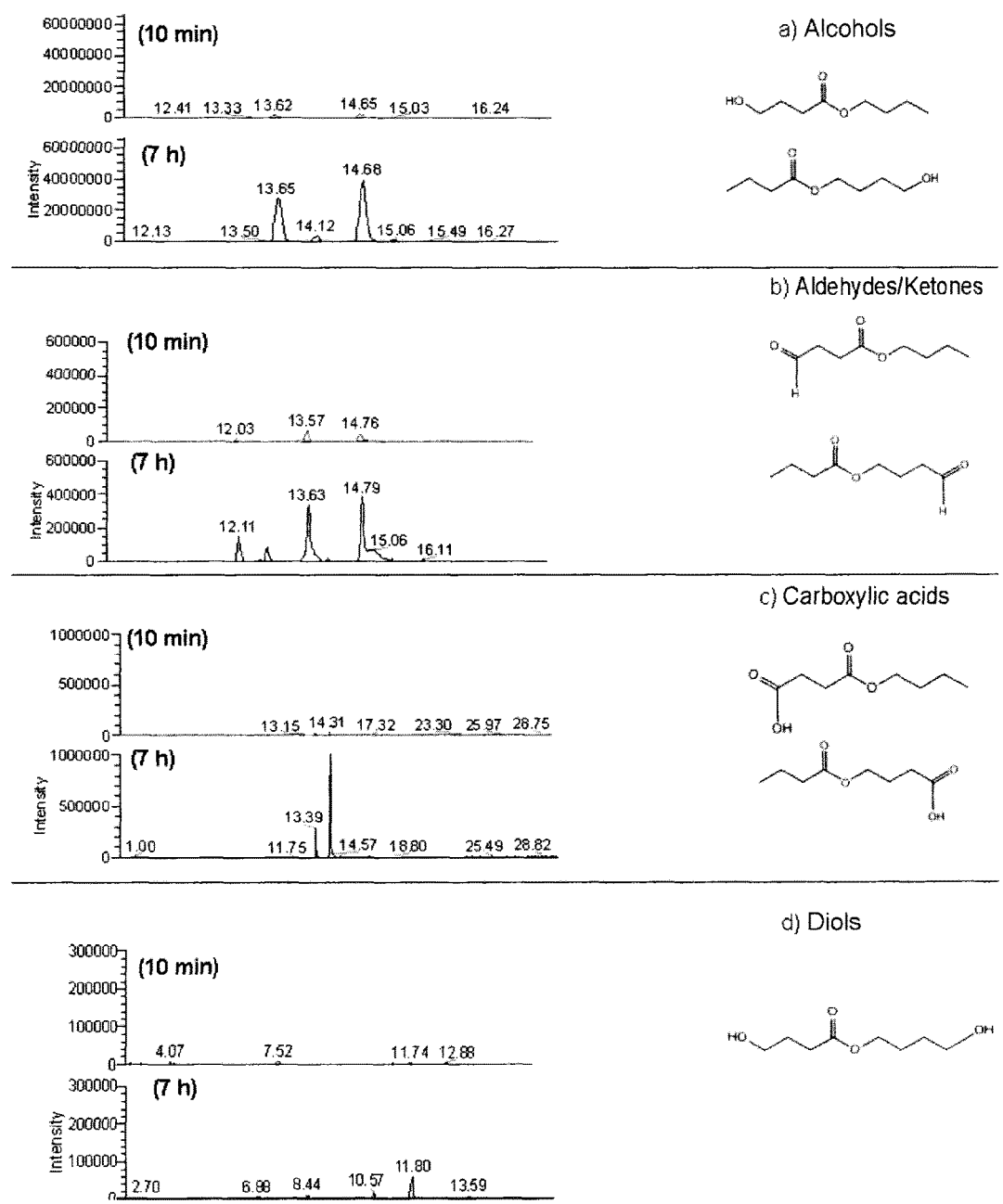
FIG. 3 shows the mass traces of the HPLC-MS analysis of the oxidation products of butyl butyrate using *E. coli* W3110 pBT10 with a comparison of the 10 min sample with the 7 h sample, resulting from Example 2.

Screening for oxidation products of butyl butyrate was conducted by HPLC-ESI-MS (Thermo Fisher Scientific). Due to their accurate masses and the empirical formulae derived therefrom, butyl butyrate and the oxidation products arising therefrom could be identified. In both experimental batches, the mono- and bis-terminally hydroxylated esters, inter alia, could be detected (see FIGS. 2 and 3).

EXAMPLE 3

Reductive Hydrogenation of the Oxidized Butyl Butyrate to Form 1,4-butanediol:

740 mg of lithium aluminium hydride are charged in 50 mL of dry diethyl ether and 10 g of the oxidized ester from Example 2 are slowly added dropwise at 0° C. After addition is complete, the mixture is heated to boiling and stirred under reflux until complete conversion.

The resulting alcohols are separated by distillation. 7.41 g of 1,4-butanediol and 1.77 g of 1-butanol are obtained. The butanol is recycled to Example 1d and esterified therein.

The invention claimed is:

1. A process for producing an α,ω-alkanediol comprising:
   a) reacting an alkanoic acid with an alkanol to give an ester,
   b) oxidizing at least one terminal carbon atom of the ester by contacting with a whole-cell catalyst, which expresses an alkane hydroxylase, in aqueous solution and in the presence of molecular oxygen, to give an oxidized ester,
   c) hydrogenating the oxidized ester to form an α,ω-alkanediol and alkanol, and
   d) removing the alkanol by distillation, forming a reaction mixture depleted with respect to the alkanol, and
   e) recycling the alkanol in a).

2. Process according to claim 1, wherein the alkanoic acid in a) is an alkanoic acid of the formula $H_3C-(CH_2)_n-COOH$, and where n>0.

3. Process according to claim 1, wherein the alkanoic acid is butanoic acid.

4. Process according to claim 1, wherein the alkanoic acid in a) is a carboxylated cycloalkane of the formula $C_nH_{2n-1}COOH$, where n>4.

5. Process according to claim 1, wherein the alkanol is an alkanol of the formula $C_nOH_{2n+2}$ and n>0.

6. Process according to claim 1, wherein the alkanoic acid and the alkanol in a) have the same carbon skeleton.

7. Process according to claim 1, wherein the whole-cell catalyst in b) expresses at least one alkane hydroxylase selected from the group consisting of AlkB from *Pseudomonas putida* comprising the sequence of SEQ ID NO: 1, a variant having at least 70% identity to SEQ ID NO: 1, CYP153 from *Alcanivorans borkumen* SK2 comprising the sequence of SEQ ID NO: 2, and a variant having at least 70% identity to SEQ ID NO: 2.

8. Process according to claim 1, wherein a) is carried out by acid-catalysed ester formation.

9. Process according to claim 1, wherein a) is carried out in aqueous solution by contacting the alkanoic acid and alkanol with an esterase, protease or lipase.

10. Process according to claim 1, wherein the alkanoic acid in a) is provided by oxidizing an alkane to the alkanoic acid.

11. Process according to claim 2, wherein n is 2 to 16.

12. Process according to claim 4, wherein n is 5 to 8.

13. Process according to claim 8, wherein a) is carried out in the presence of an organic solvent.

14. Process according to claim 9, wherein a) is carried out in aqueous solution by contacting with an esterase, protease or lipase in the form of a whole-cell catalyst expressing the esterase or lipase.

15. The process of claim 1, wherein the whole cell catalyst expresses an alkane hydroxylase that is AlkB from *Pseudomonas putida* comprising the sequence of SEQ ID NO: 1 or a variant having at least 95% identity to SEQ ID NO: 1.

16. The process of claim 1, wherein the whole cell catalyst expresses an alkane hydroxylase that is CYP153 from *Alcanivorans borkumensis* SK2 comprising the sequence of SEQ ID NO: 2 or a variant having at least 95% identity to SEQ ID NO: 2.

* * * * *

SEQUENCE LISTING

```
<160> NUMBER OF SEQ ID NOS: 2

<210> SEQ ID NO 1
<211> LENGTH: 401
<212> TYPE: PRT
<213> ORGANISM: Pseudomonas putida

<400> SEQUENCE: 1

Met Leu Glu Lys His Arg Val Leu Asp Ser Ala Pro Glu Tyr Val Asp
1               5                   10                  15

Lys Lys Lys Tyr Leu Trp Ile Leu Ser Thr Leu Trp Pro Ala Thr Pro
            20                  25                  30

Met Ile Gly Ile Trp Leu Ala Asn Glu Thr Gly Trp Gly Ile Phe Tyr
        35                  40                  45

Gly Leu Val Leu Leu Val Trp Tyr Gly Ala Leu Pro Leu Leu Asp Ala
    50                  55                  60

Met Phe Gly Glu Asp Phe Asn Asn Pro Pro Glu Glu Val Val Pro Lys
65                  70                  75                  80

Leu Glu Lys Glu Arg Tyr Tyr Arg Val Leu Thr Tyr Leu Thr Val Pro
                85                  90                  95

Met His Tyr Ala Ala Leu Ile Val Ser Ala Trp Trp Val Gly Thr Gln
            100                 105                 110

Pro Met Ser Trp Leu Glu Ile Gly Ala Leu Ala Leu Ser Leu Gly Ile
        115                 120                 125

Val Asn Gly Leu Ala Leu Asn Thr Gly His Glu Leu Gly His Lys Lys
    130                 135                 140

Glu Thr Phe Asp Arg Trp Met Ala Lys Ile Val Leu Ala Val Val Gly
145                 150                 155                 160

Tyr Gly His Phe Phe Ile Glu His Asn Lys Gly His His Arg Asp Val
```

```
                    165                 170                 175
Ala Thr Pro Met Asp Pro Ala Thr Ser Arg Met Gly Glu Ser Ile Tyr
                180                 185                 190

Lys Phe Ser Ile Arg Glu Ile Pro Gly Ala Phe Ile Arg Ala Trp Gly
            195                 200                 205

Leu Glu Glu Gln Arg Leu Ser Arg Arg Gly Gln Ser Val Trp Ser Phe
        210                 215                 220

Asp Asn Glu Ile Leu Gln Pro Met Ile Ile Thr Val Ile Leu Tyr Ala
225                 230                 235                 240

Val Leu Leu Ala Leu Phe Gly Pro Lys Met Leu Val Phe Leu Pro Ile
                245                 250                 255

Gln Met Ala Phe Gly Trp Trp Gln Leu Thr Ser Ala Asn Tyr Ile Glu
                260                 265                 270

His Tyr Gly Leu Leu Arg Gln Lys Met Glu Asp Gly Arg Tyr Glu His
                275                 280                 285

Gln Lys Pro His His Ser Trp Asn Ser Asn His Ile Val Ser Asn Leu
                290                 295                 300

Val Leu Phe His Leu Gln Arg His Ser Asp His His Ala His Pro Thr
305                 310                 315                 320

Arg Ser Tyr Gln Ser Leu Arg Asp Phe Pro Gly Leu Pro Ala Leu Pro
                325                 330                 335

Thr Gly Tyr Pro Gly Ala Phe Leu Met Ala Met Ile Pro Gln Trp Phe
                340                 345                 350

Arg Ser Val Met Asp Pro Lys Val Val Asp Trp Ala Gly Gly Asp Leu
                355                 360                 365

Asn Lys Ile Gln Ile Asp Asp Ser Met Arg Glu Thr Tyr Leu Lys Lys
                370                 375                 380

Phe Gly Thr Ser Ser Ala Gly His Ser Ser Ser Thr Ser Ala Val Ala
385                 390                 395                 400

Ser

<210> SEQ ID NO 2
<211> LENGTH: 470
<212> TYPE: PRT
<213> ORGANISM: Alcanivorax borkumensis SK2

<400> SEQUENCE: 2

Met Ser Thr Ser Ser Ser Thr Ser Asn Asp Ile Gln Ala Lys Ile Ile
1               5                   10                  15

Asn Ala Thr Ser Lys Val Val Pro Met His Leu Gln Ile Lys Ala Leu
                20                  25                  30

Lys Asn Leu Met Lys Val Lys Arg Lys Thr Ile Gly Thr Ser Arg Pro
            35                  40                  45

Gln Val His Phe Val Glu Thr Asp Leu Pro Asp Val Asn Asp Leu Ala
        50                  55                  60

Ile Glu Asp Ile Asp Thr Ser Asn Pro Phe Leu Tyr Arg Gln Gly Lys
65                  70                  75                  80

Ala Asn Ala Tyr Phe Lys Arg Leu Arg Asp Glu Ala Pro Val His Tyr
                85                  90                  95

Gln Lys Asn Ser Ala Phe Gly Pro Phe Trp Ser Val Thr Arg Tyr Glu
            100                 105                 110

Asp Ile Val Phe Val Asp Lys Ser His Asp Leu Phe Ser Ala Glu Pro
        115                 120                 125

Gln Ile Ile Leu Gly Asp Pro Pro Glu Gly Leu Ser Val Glu Met Phe
```

```
                130                 135                 140
Ile Ala Met Asp Pro Pro Lys His Asp Val Gln Arg Arg Ala Val Gln
145                 150                 155                 160

Gly Val Val Ala Pro Lys Asn Leu Lys Glu Met Glu Gly Leu Ile Arg
                165                 170                 175

Lys Arg Thr Gly Asp Val Leu Asp Ser Leu Pro Leu Asp Thr Pro Phe
                180                 185                 190

Asn Trp Val Pro Val Val Ser Lys Glu Leu Thr Gly Arg Met Leu Ala
                195                 200                 205

Ser Leu Leu Asp Phe Pro Tyr Asp Glu Arg Glu Lys Leu Val Gly Trp
        210                 215                 220

Ser Asp Arg Leu Ser Gly Ala Ser Ser Ala Thr Gly Gly Glu Phe Thr
225                 230                 235                 240

Asn Glu Asp Val Phe Phe Asp Asp Ala Ala Asp Met Ala Trp Ala Phe
                245                 250                 255

Ser Lys Leu Trp Arg Asp Lys Glu Ala Arg Gln Lys Ala Gly Glu Glu
                260                 265                 270

Pro Gly Phe Asp Leu Ile Ser Met Leu Gln Ser Asn Glu Asp Thr Lys
                275                 280                 285

Asp Leu Ile Asn Arg Pro Leu Glu Phe Ile Gly Asn Leu Ala Leu Leu
                290                 295                 300

Ile Val Gly Gly Asn Asp Thr Thr Arg Asn Ser Met Ser Gly Gly Val
305                 310                 315                 320

Leu Ala Leu Asn Gln Phe Pro Glu Gln Phe Glu Lys Leu Lys Ala Asn
                325                 330                 335

Pro Lys Leu Ile Pro Asn Met Val Ser Glu Ile Ile Arg Trp Gln Thr
                340                 345                 350

Pro Leu Ala Tyr Met Arg Arg Val Ala Lys Gln Asp Val Glu Leu Asn
                355                 360                 365

Gly Gln Thr Ile Lys Lys Gly Asp Arg Val Leu Met Trp Tyr Ala Ser
        370                 375                 380

Gly Asn Gln Asp Glu Arg Lys Phe Glu Asn Pro Glu Gln Phe Ile Ile
385                 390                 395                 400

Asp Arg Lys Asp Thr Arg Asn His Val Ser Phe Gly Tyr Gly Val His
                405                 410                 415

Arg Cys Met Gly Asn Arg Leu Ala Glu Leu Gln Leu Arg Ile Leu Trp
                420                 425                 430

Glu Glu Leu Leu Pro Arg Phe Glu Asn Ile Glu Val Ile Gly Glu Pro
        435                 440                 445

Glu Arg Val Gln Ser Asn Phe Val Arg Gly Tyr Ser Lys Met Met Val
        450                 455                 460

Lys Leu Thr Ala Lys Lys
465                 470
```